United States Patent [19]

Spector

[11] Patent Number: 5,569,511
[45] Date of Patent: Oct. 29, 1996

[54] FRAGRANCE-EMITTING DECORATIVE OBJECT

[76] Inventor: Donald Spector, 380 Mountain Rd., Union City, N.J. 07080

[21] Appl. No.: 391,545

[22] Filed: Feb. 21, 1995

[51] Int. Cl.⁶ .............................. A47G 33/08; A61K 7/46
[52] U.S. Cl. .................... 428/11; 156/61; 156/86; 428/24; 428/905
[58] Field of Search ............... 428/11, 24, 905; 156/61, 86

[56] References Cited

U.S. PATENT DOCUMENTS

| | | | |
|---|---|---|---|
| 3,829,348 | 8/1974 | Spiegel et al. | 156/86 X |
| 4,188,443 | 2/1980 | Mueller et al. | 428/335 X |
| 4,476,171 | 10/1984 | Takeuchi | 428/905 X |
| 4,696,844 | 9/1987 | Spector | 428/46 |
| 4,883,692 | 11/1989 | Spector | 428/17 X |
| 4,996,087 | 2/1991 | Rebstock | 428/11 |
| 5,328,743 | 7/1994 | Wynne et al. | 428/113 X |

*Primary Examiner*—Henry F. Epstein
*Attorney, Agent, or Firm*—Michael Ebert

[57] ABSTRACT

A decorative three-dimensional figure or other shaped object clad in a transparent, synthetic plastic film conforming to the contours of the object and exuding a fragrance whose scent is appropriate to the nature of the object. Thus when the object is a Christmas tree ornament, the fragrance may then simulate the aroma of pine needles. To clad the object it is first enveloped in a foraminated sheet of shrink wrap film that is impregnated with a volatile liquid fragrance, the sheet then being heated to cause it to shrink and conform to the contours of the object whereby the clad object then proceeds to emit the fragrance for a prolonged period.

6 Claims, 1 Drawing Sheet

FRAGRANCE-EMITTING DECORATIVE OBJECT

BACKGROUND OF INVENTION

1. Field of Invention

This invention relates generally to decorative, shaped objects that exude a fragrance, and more particularly to a technique for cladding the object with a transparent film of synthetic plastic material that conforms to the contours of the object and emits a fragrance whose scent is appropriate to the nature of the object.

2. Status of Prior Art

The aroma of perfumes and perfume-based products such as colognes and toilet waters was originally derived from the essential oils of plants. However, since the early 19th centry, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol or other solvents.

The Spector U.S. Pat. No. 4,883,692 discloses a decorative figure or other shaped object molded of foam plastic material having dispersed throughout its cellular structure a volatile liquid fragrance. When exposed to the atmosphere, the figure then continuously exudes the fragrance for a prolonged period, the figure proceeding to shrink as a result of liquid loss.

The present invention resides in a decorative, three-dimensional figure or other shaped object molded of plastic or other non-porous material, the object being clad with a transparent shrink wrap film that conforms to the contours of the object and exudes a fragrance. Hence of prior art background interest are patents relating to shrink wrap film, such as the patent to Mueller et al. U.S. Pat. No. 4,188,443 which discloses a multi-layer shrink wrap film. Also the patent to Wynn et al. U.S. Pat. No. 5,328,743 disclosing a tear-resistant reinforced shrink wrap film.

Of particular interest is the patent to Shah U.S. Pat. No. 5,175,142 which stresses the desirability of having a shrink wrap film—with low mousture permeability. In contradistinction, a shrink wrap film in accordance with the invention is porous and therefore has a high moisture permeability.

The two major families of plastic resins from which commercially available shrink films are made are made for wrapping purposes are the polyolefins and polyvinyl chlorides. The distinguishing characteristic of a shrink film lies in its ability to shrink when exposed to some level of heat, or if the film itself is restrained, to create shrink tension within the film.

This ability is exploited by passing the object wrapped in shrink film through a hot air tunnel, thereby causing the film to shrink around the product to produce a tight, transparent cover that conforms to the contours of the product. Typical items wrapped in PVC or polyolefin shrink films are toys, sporting goods, hardware, household products and industrial parts.

SUMMARY OF INVENTION

In view of the foregoing, the main object of this invention is to provide a three-dimensional decorative figure or other shaped object that is protectively clad in a transparent synthetic plastic film that conforms to the contours of the object and exudes a fragrance whose aroma is appropriate to the nature of the object.

More particularly, an object of the invention is to provide a technique for producing a clad object of the above type by means of a shrink wrap film impregnated with a volatile fragrance.

A significant feature of the invention is that it renders a conventional shrink wrap film moisture permeable so that it may be impregnated with a volatile fragrance and retain this fragrance after the film has been heat shrunk.

Briefly stated, these objects are attained by a decorative three-dimensional figure or other shaped object clad in a transparent, synthetic plastic film conforming to the contours of the object and exuding a fragrance whose scent is appropriate to the nature of the object. Thus when the clad object is a Christmas tree ornament, it then exudes the scent of pine needles. To clad the object, it is first enveloped in a foraminated sheet of shrink wrap film impregnated with a volatile liquid fragrance, the sheet then being heated to cause it to shrink and conform to the contours of the object whereby the clad object then proceeds to emit the fragrance for a prolonged period.

BRIEF DESCRIPTION OF THE DRAWINGS

For a better understanding of the invention reference is made to the detailed description to follow which is to be read in conjunction with the accompanying drawings of which.

DESCRIPTION OF INVENTION

Figure 1:
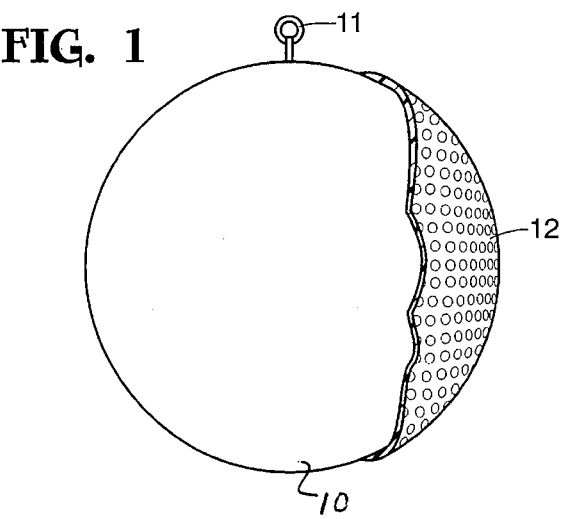
FIG. 1 illustrates a Christmas tree ornament that is protectively clad in accordance with the invention.

The present invention is applicable to any shaped three-dimensional decorative object that lends itself to being protectively clad in a shrink wrap film that conforms to the contours of the shaped object. While the invention will be illustrated in the drawing in connection with a Christmas tree ornament and with a toy figure or doll, these are but two examples of how the invention can be realized in practice.

Figure 2:
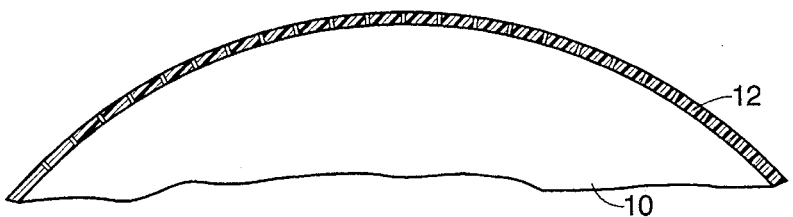
FIG. 2 is a section taken through the film cladding the ornament.

FIGS. 1 and 2 show a ball-shaped Christmas tree ornament 10 provided with a mounting loop 11 to suspend the ornament from a tree. The ball which has a highly reflective metallized color finish as is customary in Christmas tree ornaments, is protectively clad in a transparent film 12 of synthetic plastic material which comforms to the ball and effectively reenforces it without however changing its decorative appearance. A Christmas tree ornament is usually somewhat fragile, and the cladding makes it much less so.

Film 12 is impregnated with a volatile fragrance whose scent is appropriate to a Christmas tree or to the Christmas Season. Thus the scent exuded from the film may be that of pine needles, or of a burning wood fire. With modern fragrance technology, it is possible to simulate virtually all natural odors, including those which may be offensive rather than pleasing.

In order to clad the ornament, use is made for this purpose of a sheet of transparent shrink film impregnated with the volatile fragrance to be emitted from the film. A conventional shrink film formed of PVC, polyolefin or other synthetic plastic material having shrink characteristics is impermeable to liquids and cannot be impregnated with a liquid fragrance.

Figure 3:
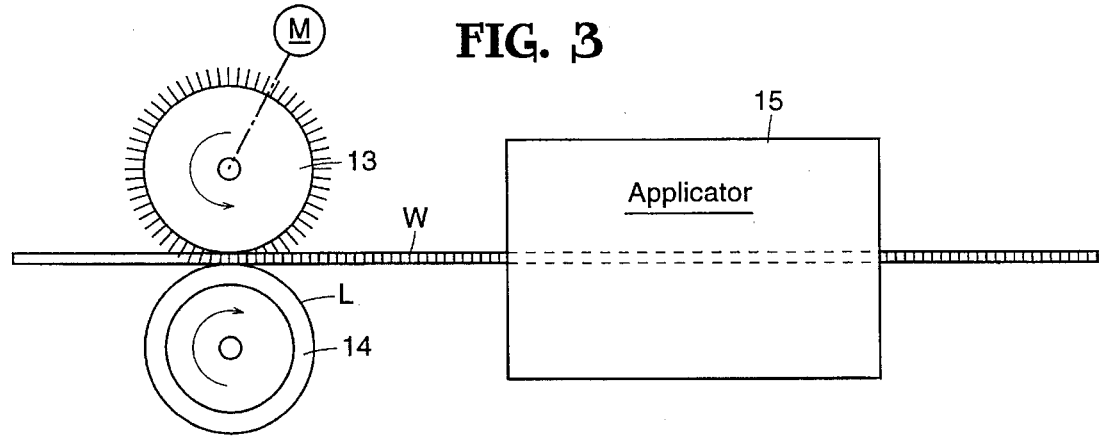
FIG. 3 illustrates schematically how the shrink film is foraminated.

In order, therefore, to render the shrink wrap film liquid permeable, it is foraminated in the manner illustrated in FIG. 3 in which a web W of shrink wrap film is fed between cooperating rolls 13 and 14 in a foraminating station. The upper roll 13 which is driven by a motor M is provided with a circumferential array of fine pins which penetrate the film. The film is backed by the lower roll 14 that is covered by outer layer L of elastomeric material.

Thus needled into the shrink wrap film is a myriad of fine pores which render the film porous. The foraminated film is then conducted through an applicator station 15 in which the liquid fragrance contained in a well is transferred by rollers to the film. The fragrance having absorbed by the foraminated film and is retained in the pores by capillary attraction.

After the ornament is enveloped in a sheet of fragrance-impregnated shrink film, it is conducted through a hot air tunnel whose atmospheric temperature is at a level sufficient to effect shrinking of the film about the object so that it conforms to the contours of the ornament and thereby protectively clads the ornament. While the heat in the tunnel may volatilize some of the liquid fragrance in causing the film to shrink it densifies the pores to enhance the retention of the fragrance.

Emission of the fragrance from the fragrance-impregnated shrink film only occurs at the pore outlets on the outer surface of the film, for the inner face of the film tightly engages the surface of the object, thereby blocking emission from the inner face. Thus the discharge of fragrance from the film is controlled and the clad object continues to emit fragrance for a prolonged period.

Figure 4:
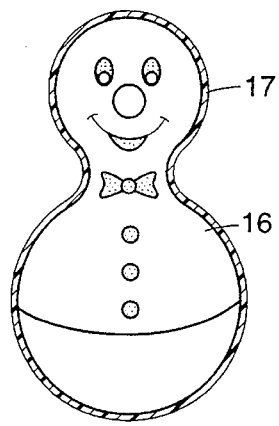
FIG. 4 shows a clad three-dimensional figure in accordance with the invention.

FIG. 4 shows a doll-like toy FIG. 16 molded or otherwise formed of a rigid, non-porous synthetic plastic material, such as PVC. The figure is clad by a foraminated transparent shrink film 17 impregnated with a liquid fragrance, the scent of which is appropriate to the figure. Thus if the figure is that of an infant, the scent may be that of talcum powder, or any other scent one usually associates with an infant.

The complementary relation ship between the nature of the object and the fragrance exuded therefrom may be exploited for educational purposes as well as for amusement. One could produce for example a set of miniature molded plastic figures of different animals (tiger, lion, horse, hippo, etc.) and clad each figure in a shrink film emitting an odor simulating the natural order of the animal and thereby provide, as it were, a private zoo for a child. Thus one who walks through the several animal halls of a zoo not only sees a variety of caged animals, but also is exposed to their characteristic odors. The smell of these animals is an unforgetable constituent of a zoo experience.

Or one could provide a set of rigid plastic balls each having printed on its spherical surface a different flower in appropriate colors. The balls would all be clad in shrink film exuding a fragrance simulating that of the scent of the flower displayed by each ball. In this way one would provide a child with a set of flower balls, who from their respective aromas then learns to distinguish the distinctive fragrances of these flowers.

The normal function of a conventional shrink wrap film is to seal the wrapped object against moisture and dirt; hence the film is impermeable to moisture. In contradistinction a foraminated shrink wrap film in accordance with the invention is not moisture impermeable, but has sufficient porosity to absorb a liquid fragrance, so that the clad object exudes an aroma whose scent is appropriate to the nature of the object clad thereby.

While there has been shown a preferred embodiment of a fragrance-emitting decorative object in accordance with the invention, it will be appreciated that many changes may be made therein without departing from the spirit of the invention.

I claim:

1. An aroma-generating object comprising:

A. a three-dimensional decorative shaped object; and

B. a transparent, liquid-impermeable, synthetic-plastic shrink film conforming to the contours of the shaped object to form a protective cladding therefor, said film being foraminated to create fine pores, and a volatile liquid fragrance impregnating the pores that is exuded therefrom for a prolonged period.

2. An object as set forth in claim 1, in which the aroma of the fragrance is appropriate to the nature of the object.

3. An object as set forth in claim 2, in which the object is a plastic ball having printed on its spherical surface a design which resembles a particular flower and the fragrance emulates the natural scent thereof.

4. A technique for producing an object as set forth in claim 1, said technique comprising the steps of foraminating a sheet of shrink film to form myriad pores therein which are then impregnated with said liquid fragrance, enveloping the object in said impregnated sheet of said shrink film, and then heating the film to cause it to shrink to conform to the contours of the object.

5. A method for producing an aroma-emitting shaped object having a recognizable nature, comprising the steps of:

A. enveloping the object in a foraminated sheet of transparent shrink film whose pores are impregnated with a volatile fragrance whose aroma is appropriate to the nature of the object; and B. heating the sheet to cause it to shrink and conform to the contours of the object, thereby protectively cladding the object and causing it to exude an aroma.

6. A method as set forth in claim 5, in which the object is a Christmas tree ornament and the aroma is that of pine needles.

* * * * *